US012599625B2

(12) United States Patent
Williams

(10) Patent No.: US 12,599,625 B2
(45) Date of Patent: Apr. 14, 2026

(54) TREATMENT OF ARDS AND OTHER CONDITIONS CAUSED BY ACUTELY ELEVATED CYTOKINE LEVELS AND POST ARDS CHRONIC CYTOKINE PRODUCTION USING INHALED ANESTHETICS

(71) Applicant: Penland Foundation, Beaumont, TX (US)

(72) Inventor: Roland M. Williams, Beaumont, TX (US)

(73) Assignee: Penland Foundation, Beaumont, TX (US)

( * ) Notice: Subject to any disclaimer, the term of this patent is extended or adjusted under 35 U.S.C. 154(b) by 720 days.

(21) Appl. No.: 17/662,068

(22) Filed: May 4, 2022

(65) Prior Publication Data

US 2022/0362286 A1 Nov. 17, 2022

Related U.S. Application Data

(60) Provisional application No. 63/187,953, filed on May 13, 2021.

(51) Int. Cl.
| | |
|---|---|
| *A61K 33/00* | (2006.01) |
| *A61P 11/16* | (2006.01) |
| *G01N 33/68* | (2006.01) |

(52) U.S. Cl.
CPC .............. *A61K 33/00* (2013.01); *A61P 11/16* (2018.01); *G01N 33/6863* (2013.01)

(58) Field of Classification Search
CPC ..... A61K 33/00; A61P 11/16; G01N 33/6863; G01N 2800/125; G01N 2800/52
See application file for complete search history.

(56) References Cited

U.S. PATENT DOCUMENTS

| | | | |
|---|---|---|---|
| 6,063,768 | A | 5/2000 | First |
| 6,500,436 | B2 | 12/2002 | Donovan |
| 7,235,584 | B2 | 6/2007 | Garzon et al. |
| 8,372,976 | B2 | 2/2013 | Mortensen et al. |
| 8,399,401 | B2 | 3/2013 | Foster et al. |
| 8,697,066 | B2 | 4/2014 | Gaylis et al. |
| 9,243,301 | B2 | 1/2016 | Foster et al. |
| 9,579,299 | B2 | 2/2017 | Glozman |
| 9,945,856 | B2 | 4/2018 | van der Hoek |
| 10,064,921 | B2 | 9/2018 | Blumenfeld |
| 10,201,565 | B2 | 2/2019 | Mailova et al. |
| 10,245,305 | B2 | 4/2019 | First |
| 10,857,382 | B2 | 12/2020 | Ibrahim et al. |
| 11,065,218 | B2 | 7/2021 | Bannister et al. |
| 2002/0185126 | A1 | 12/2002 | Krebs |
| 2005/0020654 | A1 | 1/2005 | Pershadsingh et al. |
| 2005/0152905 | A1 | 7/2005 | Omoigui |
| 2005/0267009 | A1 | 12/2005 | Deagle |
| 2006/0178354 | A1 | 8/2006 | Lucas |
| 2009/0071481 | A1 | 3/2009 | Fishman |
| 2009/0232849 | A1 | 9/2009 | Gallez et al. |

| | | | |
|---|---|---|---|
| 2009/0324678 | A1 | 12/2009 | Thorne et al. |
| 2012/0207733 | A1 | 8/2012 | Jacky et al. |
| 2012/0207742 | A1 | 8/2012 | Jacky et al. |
| 2013/0095194 | A1* | 4/2013 | Bessiere ................ A61P 39/00 424/600 |
| 2013/0177548 | A1 | 7/2013 | Shaari |
| 2013/0302445 | A1 | 11/2013 | Barbut et al. |
| 2015/0197739 | A1 | 7/2015 | James et al. |
| 2016/0067276 | A1* | 3/2016 | Polizzotti .......... A61K 41/0028 44/457 |
| 2016/0243232 | A1 | 8/2016 | Pickett |
| 2017/0049866 | A1 | 2/2017 | Sanders |
| 2017/0136105 | A1 | 5/2017 | Ho et al. |
| 2017/0246267 | A1 | 8/2017 | Wang et al. |
| 2018/0235931 | A1 | 8/2018 | Basta et al. |
| 2018/0243373 | A1 | 8/2018 | Hamed |

(Continued)

FOREIGN PATENT DOCUMENTS

| | | |
|---|---|---|
| AU | 2011203062 | 1/2013 |
| CN | 101031317 | 7/2012 |

(Continued)

OTHER PUBLICATIONS

Turan et al., Nitrous Oxide for the Treatment of Chronic Low Back Pain, Anesthesia & Analgesia, Nov. 2015, vol. 121, No. 5, pp. 1350-1359.

Lightigfeld ct al., The treatment of alcoholic withdrawal states with oxygen and nitr0us oxide, South African Medical Journal, Mar. 6, 1982, vol. 61, Iss. 349, pp. 349-351.

Park et al., Cytokine Balance in the Lungs of Patients with Acute Respiratory Distress Syndrome, American Journal of Respiratory and Critical Care Medicine, Nov. 1, 2011, vol. 164, Iss. 10, pp. 1896-1903.

Rao et al., Comparison of five equations for estimating resting energy expenditure in Chinese young, normal weight healthy adults, European Journal of Medical Research, Sep. 1, 2012, vol. 17, Iss. 26, pp. 1-9.

(Continued)

*Primary Examiner* — Snigdha Maewall
(74) *Attorney, Agent, or Firm* — Fox Rothschild LLP

(57) ABSTRACT

Nitrous oxide and oxygen for use in treating ARDS caused by viral and bacterial infections, injuries, or other conditions that have resulted in acute, excess activation of the cytokine system in a patient in need thereof is provided. The treatment comprises administering nitrous oxide and oxygen to the patient by inhalation before, during, and/or after ARDS occurs. It is also applicable for treating, alleviating, and/or preventing an aftereffect of said conditions. A composition, duration, an interval, and a total amount of nitrous oxide and oxygen depend on each patient's individual situation and needs. Inhalation of nitrous oxide and oxygen can also stop the post ARDS symptoms that remain after an acute ARDS condition such as, but not limited to viral infections, bacterial infections, injuries, or any condition that results from any cytokine storm. Inhalation of nitrous oxide and oxygen can also treat local cytokine damages caused by said conditions.

22 Claims, No Drawings

(56)                    References Cited

U.S. PATENT DOCUMENTS

| | | | |
|---|---|---|---|
| 2018/0296582 A1 | 10/2018 | von Maltzahn et al. |
| 2018/0296732 A1 | 10/2018 | Kutryk |
| 2019/0127718 A1 | 5/2019 | Madec et al. |
| 2019/0185837 A1 | 6/2019 | Jacky et al. |
| 2019/0298779 A1 | 10/2019 | Falb et al. |
| 2019/0314470 A1 | 10/2019 | Khavari et al. |
| 2019/0315836 A1 | 10/2019 | Delahay |
| 2020/0046813 A1 | 2/2020 | Borodic |
| 2020/0056145 A1 | 2/2020 | Brown et al. |
| 2020/0360483 A1 | 11/2020 | Dong et al. |
| 2020/0368365 A1 | 11/2020 | Ruoslahti et al. |
| 2021/0121541 A1 | 4/2021 | Brin et al. |
| 2021/0130445 A1 | 5/2021 | Brin |
| 2021/0177823 A1 | 6/2021 | Weinstein et al. |
| 2021/0177946 A1 | 6/2021 | Sanders |
| 2021/0205415 A1 | 7/2021 | Shandler et al. |
| 2021/0205422 A1 | 7/2021 | Kalinichev et al. |
| 2021/0252033 A1 | 8/2021 | Painter et al. |

FOREIGN PATENT DOCUMENTS

| | | | | |
|---|---|---|---|---|
| CN | 105147608 | 12/2015 | | |
| EP | 1187635 | 2/2004 | | |
| EP | 1807118 | 7/2007 | | |
| EP | 1890714 | 2/2008 | | |
| EP | 1919892 | 5/2008 | | |
| EP | 2012811 | 1/2009 | | |
| EP | 2200999 | 6/2010 | | |
| EP | 2610244 | 7/2013 | | |
| EP | 2279196 | 1/2015 | | |
| EP | 2985281 | 2/2016 | | |
| EP | 2667854 | 1/2019 | | |
| EP | 3689331 | 8/2020 | | |
| KR | 20170014106 | 2/2017 | | |
| WO | 0155304 | 8/2001 | | |
| WO | 0276177 | 10/2002 | | |
| WO | 2005009437 | 2/2005 | | |
| WO | 2006018655 | 2/2006 | | |
| WO | 2008064552 | 6/2008 | | |
| WO | WO-2011112283 A1 * | 9/2011 | .......... | A61M 11/006 |
| WO | 2014/053651 | 4/2014 | | |
| WO | 2018/129404 | 7/2018 | | |
| WO | 2019051380 | 3/2019 | | |
| WO | 2019075263 | 4/2019 | | |
| WO | 2019191752 | 10/2019 | | |
| WO | 2020010123 | 1/2020 | | |
| WO | 2020065249 | 4/2020 | | |
| WO | 2020117564 | 6/2020 | | |
| WO | 2020218823 | 10/2020 | | |
| WO | 2021101902 | 5/2021 | | |
| WO | 2021113311 | 6/2021 | | |
| WO | 2021163222 | 8/2021 | | |

OTHER PUBLICATIONS

Aguirre-Siancas, "Substance P, proinflammatory cytokines, transient receptor potential vanilloid subtype 1 and COVID-19: a working hypothesis," Neurología, 36, pp. 169-189 (2021).

Australian Dental Association, "The Use of Nitrous Oxide During COVID-19," available online at <https://www.ada.org.au/Covid-19-Portal/Cards/Misc/Infection-Control-Cards/The-Use-of-Nitrous-Oxide-During-COVID-19>, 2 pages (2020).

Fleischmann, "Nitrous oxide may not increase the risk of cancer recurrence after colorectal surgery: a follow-up of a randomized controlled trial," BMC Anesthesiology, (2009).

International Search Report and Written Opinion for International Patent Application No. PCT/US2022/072228, mailed Jul. 29, 2022 (8 pages).

Ishikawa, "Nitrous Oxide Decreases Substance P Receptor Binding in The Rat Spinal Cord," Journal of Neurosurgical Anesthesiology, 1(4), pp. 316-322 (1989).

Takasusuki et al., "Effects of General Anesthetics on Substance P Release and c-Fos Expression in the Spinal Dorsal Horn," Anesthesiology, 119, pp. 433-442 (2013).

Lassen and Kristensen, "Remission in Chronic Myeloid Leucemia Following Prolonged Nitrous Oxide Inhalation," Danish Medical Bulletin, vol. 6, No. 8, pp. 252-255 (1959).

Lotz et al., "Effects of inhaled nitric oxide in COVID-19—induced ARDS—Is it worthwhile?" Acta Anaesthesiol. Scand., 65, pp. 629-632 (2021).

Manigandan et al., "A review on role of nitrous oxide nanoparticles, potential vaccine targets, drug, health care and artificial intelligence to combat COVID-19," Applied Nanoscience, 8 pages (2021).

Mehboob, "Aprepitant as a combinant with Dexamethasone reduces the inflammation via Neurokinin 1 Receptor Antagonism in severe to critical Covid-19 patients and potentiates respiratory recovery: A novel therapeutic approach," 13 pages (2020).

Miller et al., "Inhalational Anesthetic," StatPearls Publishing, Treasure Island (FL); 10 pages (2021).

Wiley, "Use of nitrous oxide-oxygen inhalation sedation in the COVID-19 era," Int. J. Paediatr. Dent., 31, pp. 433-435 (2021).

Molina et al., "Nitrous oxide inhalant abuse and massive pulmonary embolism in COVID-19," American Journal of Emergency Medicine, 38(7), 2 pages, 1549.e1-1549.e2 (2020).

National Cancer Institute, "Cancer Pain (PDQ®)—Health Professional Version," available online at <https://www.cancer.gov/about-cancer/treatment/side-effects/pain/pain-hp-pdq>; Updated Sep. 2, 2022, 89 pages.

National Cancer Institute, "Nitric Oxide Releasing Solutions to Prevent and Treat Mild/Moderate COVID-19 Infection (NOCOVID)," available online at <https://clinicaltrials.gov/ct2/show/NCT04337918>; First Posted: Apr. 8, 2020; Last Update Posted: Feb. 10, 2021, (11 pages).

Nowaczyk et al., "Carbon Monoxide and Nitric Oxide as Examples of the Youngest Class of Transmitters," Int. J. Mol. Sci., 22(6029), 25 pages (2021).

Patyar et al., "Bacteria in cancer therapy: a novel experimental strategy," Journal of Biomedical Science vol. 17(21), 9 pages (2010).

Koblin, "Nitrous Oxide: A Cause of Cancer or Chemotherapuetic Adjvant?" Seminars in Surgical Oncology, vol. 6 No. 3, pp. 141-147 (1990).

Jung et al., "Growth suppression of four cancer cells by hyerbaric nitrous oxide and methotrexate," Korean Journal of Anesthesiology, vol. 58, No. 1, pp. 61-69 (2010).

* cited by examiner

TREATMENT OF ARDS AND OTHER CONDITIONS CAUSED BY ACUTELY ELEVATED CYTOKINE LEVELS AND POST ARDS CHRONIC CYTOKINE PRODUCTION USING INHALED ANESTHETICS

CROSS-REFERENCE TO RELATED APPLICATION

The application is based on and claims the benefit of U.S. Provisional Application No. 63/187,953, filed May 13, 2021, the entirety of which is incorporated by reference.

TECHNICAL FIELD

Embodiments of the present disclosure generally relate to methods for treating, alleviating, and/or preventing Acute Respiratory Distress Syndrome (ARDS) caused by the acute overactivation of the cytokine system (i.e., cytokine storm). ARDS can be caused by, for example, viral infections, bacterial infections, injuries, some medical treatments, acute pancreatitis, G6PD deficiency, burns, sickle anemia, causing pathological symptoms of an exaggerated cytokine response. Embodiments of the present disclosure are also related to methods for treating, alleviating and/or preventing the chronic activation of the cytokine system after recovery from ARDS. The cause of chronic inflammation includes but is not limited to altered neural signaling.

DESCRIPTION OF RELATED ART

Nitrous oxide may mitigate the acute overproduction of substance P and glutamate in the spinal and vagal sensory ganglia. Substance P activates the NK-1-3 receptors on immune cells, triggering their release of cytokines. This is a normal part of infection control and damage repair. However, overproduced Substance P may damage or destroy normal host tissue. Glutamate overproduction may cause pain, various sensory disturbance, and altered neural signaling.

Inhaled Anesthetics

An inhaled anesthetic is a chemical compound possessing general anesthetic properties that can be delivered by inhalation. Agents of current use include, but are not limited to, halothane, isoflurane, sevoflurane, desflurane, nitrous oxide, and xenon. There are dozens of other chemicals in this class of medications that currently have no current clinical use.

The inhaled anesthetics are well-known for their central sedative effects such as conscious sedation used in dentistry at lower concentrations to general anesthesia at higher concentrations. Studies show the inhaled anesthetics may also suppress the production of the tachykinins (substance P, glutamate, and CGRP) in the spinal and vagus sensory ganglia. The half-life of the tachykinins is seconds to minutes, so the effect is almost instantaneous. Unlike the central sedative effect, this suppression of the tachykinins lasts for 4-6 hours after cessation of use of the inhaled anesthetics.

When sensory nerves are damaged by an infection or injury, the neurons and the neurostructural cells around them (astrocytes, glial cells, and satellite) produce substance P, glutamate, and CGRP in response. The glutamate causes sensory hyperactivity and substance P activates receptors on immune cells producing the vast array of cytokines to fight infection or repair damage.

Some viral infections, as part of their pathogenicity, vastly overstimulate the sensory nerves causing an extreme overproduction of the tachykinins with a resulting acute pathological overproduction of the cytokines. This is called Acute Respiratory Distress Syndrome (ARDS). The overproduction of substance P may be 60-70× normal levels. Injuries such as but not limited to near drowning, inhalation of toxic substances, massive transfusions, drug toxicity, severe injury, acute pancreatitis, burns, sickle cell anemia, G6PD deficiency, etc. may trigger ARDS as well as certain viral and bacterial infections.

Clinical observation has shown that sedation-level nitrous oxide use (e.g., 50% nitrous oxide/50% oxygen) may suppress the tachykinin overproduction enough to effect clinical problems.

In the sensory system neuropathic conditions that are known to be caused by excessive glutamate production, such as migraines, fibromyalgia, anxiety, post-herpetic pain, and neuropathic pain are relieved during use of, for example, about 50% nitrous oxide/about 50% oxygen for about 20-30 minutes for as long as 6 hours.

Conditions known to be caused by substance P cytokine chronic or acute overproduction can be mitigated by sedation-level nitrous oxide administration. Clinical observation has shown that patients with symptoms of COVID-19 and asthma, which are known to be caused by acute and chronic excessive substance P, may be relieved with, for example, about 20 minutes of nitrous oxide every about 4-6 hours.

Some patients that survive a moderate to severe ARDS event may have residual symptoms such as but not limited to shortage of breath, migraines, loss of taste and smell, cardiac arrhythmia and fatigue. Conscious sedation-level nitrous oxide may mitigate or alleviate these residual ARDS symptoms, for example, after 1-3 days use of sedation-levels of 50% nitrous oxide/50 oxygen for about 20 minutes once a day.

SUMMARY

Embodiments of the present disclosure are related to nitrous oxide and oxygen for use in treating ARDS resulting from viral and bacterial infections, injuries, or other conditions that have resulted in acute and excess activation of the cytokine system in a patient in need thereof. This treatment method is also applicable for treating, alleviating, and/or preventing an aftereffect of said ARDS conditions. The method of treating the substance P related overproduction and resulting cytokine storm will be the use of nitrous oxide and oxygen by inhalation to suppress the neural and epithelial overproduction of substance P and glutamate. In some embodiments, the inhalation of nitrous oxide and oxygen may treat local cytokine damages resulting from localized acutely elevated level of cytokines. The localized accurately elevated level of cytokines may be caused by, for example, burns, poison ivy, and a bacterial or viral infection such as a shingles infection and a stomach virus.

In some embodiments, the use of nitrous oxide and oxygen by inhalation to lower the ganglia and epithelial production of substance P is provided. Other inhaled anesthetics may be used to suppress the neutrally controlled production of substance P. The inhaled anesthetics must be safe for patients to inhale. Such inhaled anesthetics may include, but not be limited to, halothane, isoflurane, sevoflurane, desflurane, nitrous oxide, xenon, or a combination thereof. The inhaled anesthetics are sub-classified as either volatile or non-volatile. The volatile anesthetics (e.g., halothane, isoflurane, sevoflurane and desflurane) are liquids at room temperature and require the use of vaporizers for inhalational administration. The non-volatile anesthetics (e.g., nitrous oxide and xenon) are in gas form at room temperature. The inhaled anesthetics described in the embodiments of the present disclosure do not encompass anesthetics (e.g., barbiturates, ketamine, propofol) administered by injections such as an intravenous injection. It does not cause respiratory depression, oversedation, or irritation of the lungs at effective dosages with little or no side effects. The inhaled dosage can be from about 1% nitrous oxide/about 99% oxygen to about 70% nitrous oxide/about 30% oxygen, depending on individual needs and sensitivity. Clinical indications suggest that about 40% nitrous oxide/about 60% oxygen to about 50% nitrous oxide/about 50% oxygen would be optimal. Other inhaled anesthetics may have to be used at a different oxygen % than the nitrous oxide to produce effective clinical results. Other aforementioned inhaled anesthetics can be included in the dosage or only the specified composition can be used. Other inhalants can be included in the above-compositions such as for other purposes.

In some embodiments, average duration of inhalation would vary from one minute to one hour, every about 4-6 hours. Duration of each treatment could vary from about one minute to about one hour. About 20 minutes per each inhalation is believed to be optimal. In general, one appointment may span about 1-4 days. For some patients, it may take about 1-4 appointments for the treatment of ARDS. The course of treatment will vary according to the condition being treated. It will depend on results of alleviating the underlying conditions that is causing the acute cytokine levels. For example, COVID-19 treatment will need to continue until the immune system produces antibodies and defeats the virus and the viral induced cytokine storm desists. The ability to vary the percentages of $N_2O/O_2$ ratio, the time of treatment and interval between treatment, and the length of time of the treatment cycles will give medical practitioners effective tools to control damaging acute cytokine conditions while the initiating cause is addressed.

A composition, a duration, an interval, and a total amount of the nitrous oxide and oxygen administered to an adult or a child can be titrated to the individual patient's needs. For example, adjustments may have to be made for age and body weight.

In some embodiments, before, during, and after the provision of nitrous oxide and oxygen by inhalation, blood tests may be done to monitor and assess the patient's cytokine level including a substance P level and a viral load. In addition, before, during and after the inhalation of nitrous oxide and oxygen, a blood oxygen level and a pulse may be monitored and assessed.

DETAILED DESCRIPTION

Further in relation to this, before explaining at least the preferred embodiments of the present disclosure in greater detail, it is to be understood that embodiments of the present disclosure are not limited in its application to the details of construction and to the arrangements of the components set forth in the following description. It would be understood by those of ordinary skill in the art that embodiments beyond those described herein are contemplated, and the embodiments can be practiced and carried out in a plurality of different ways. Also, it is to be understood that the terminology used herein is for the purpose of description and should not be regarded as a limiting factor.

Unless otherwise defined the terms used herein refer to that which the ordinary artisan would understand such term to mean based on the contextual use of such term herein. To the extent that the meaning of a term used herein as understood by the ordinary artisan based on the contextual use of such term differs in any way from any particular dictionary definition of such term, it is intended that the meaning of the term as understood by the ordinary artisan will prevail.

As used herein, "consists essentially of" when used in conjunction with a composition means excluding other materials that contribute to mitigating cytokine overproduction, thereby treating ARDS or post-ARDS symptoms. The objective of administering nitrous oxide and oxygen is to treat ARDS or post-ARDS symptoms by mitigating cytokine overproduction. With the language, other materials that contribute to the treatment that materially affect the basic and novel characteristics of embodiments of the present disclosure are not required and are potentially counterproductive because they may offset the treatment effect of nitrous oxide and oxygen. In other words, the meaning of "consists essentially of" is tied to the objective and excludes materials (that contribute to the treatment) that are pharmaceutically active for the treatment and materially mitigate cytokine overproduction and thereby affecting the treatment of ARDS or post-ARDS symptoms. Small traces that have little or no effect to the treatment as part of the embodiments of the present disclosure may exist in a composition that consists essentially of nitrous oxide and oxygen under the definition because it would not materially affect its function and/or objective.

As used herein, the term "about" means approximately or nearly and in the context of a numerical value or range set forth herein means±10% of the numerical value or range recited or claimed.

The term "treating" includes delaying, alleviating, mitigating, or reducing the intensity, progression, or worsening of one or more attendant symptoms of a disorder or condition and/or alleviating, mitigating, or impeding one or more causes of a disorder or condition. Treatment under embodiments of the present disclosure may be a preventative treatment, prophylactic treatment, remission of treating or ameliorating treatment.

The term "therapeutically effective amount" or "therapeutically effective dose" refers to the amount of a composition, compound, therapy, or course of treatment that, when administered to an individual for treating a disorder or disease, is sufficient to affect such treatment for the disorder or disease. The "therapeutically effective amount" will vary depending on the composition, the compound, the therapy, the course of treatment, the disorder or disease and its severity and the age, weight, etc., of the individual to be treated.

In accordance with the principles of embodiments of the present disclosure, use of nitrous oxide and oxygen by inhalation to treat ARDS caused by viral infections, bacterial infections, injuries, or conditions that result in excess activation of the cytokine system (i.e., cytokine storm) using nitrous oxide and oxygen by inhalation is provided.

An Exemplary Cause of ARDS is a Viral Infection from COVID-19

Cytokines/Cytokine Storm

Cytokines are a diverse group of small proteins and peptides that among other functions regulate and participate in the initial response to infection. Some have antibacterial and antiviral properties, some suppress viral and bacterial reproduction, some destroy infected cells and tissue, and others raise body temperature to suppress and slow the infection until antibody production begins.

The major types of cytokines are interferon's, interleukins, chemokines, colony-stimulating factors, and tumor necrosing factors. There are hundreds of different peptides under these major classes that damage, kill, or slow the growth of invading bacteria or viruses. They are the body's version of chemotherapy. However, this comes at the cost of some collateral damage. The stronger the cytokine reaction, the more damage to healthy tissue. Some of the body's own tissue is damaged or destroyed in its effort to slow the invasion. As antibody production starts in 3-10 days, the bacteria or viruses are disabled and marked for destruction by the antibodies and the infection is eliminated. Cytokine overproduction is slowed and eliminated. The damage to normal tissue is repaired or replaced with fibrous (scar) tissue, and the infection ceases to exist. Cells of the immune system store information about the viral or bacterial protein in memory cells. If these same foreign proteins are later introduced into the body again, antibody production may stark immediately. This is called immunity.

The cytokine reaction is initially triggered by viral or bacterial proteins and cellular damage from the infection. One of the first triggers for this is a peptide produced by the lung's epithelial cells called; substance P. Later, a much larger amount of substance P is produced and released by the sensory neurons in response to their damage by the bacterial or viral attack and the cytokine reaction. Viruses trigger an especially strong overproduction of cytokines.

When a person is infected by a virus or bacteria, three things may happen:

1) Because of the virulence of the invader, age of the person, the loss of immune function, or medical conditions, the immune system cannot control the infection and it overwhelms the body's defenses, spreading to other organs and the person dies.

2) The initial strong cytokine infection delays the infection until the body starts producing antibodies which then attach to the viruses marking it for destruction, which is eliminated without any further damage to normal tissues. The cytokine reaction is eliminated, and the infection is gone.

3) The viral or bacterial infection is suppressed or eliminated by the immune system, but the cytokine reaction (cytokine storm) does not abate, and the inflammation reaction continues. The increasing inflammation and cytokine production damage more and more tissue. The cytokines may enter the circulation, as in the case of ARDS, and damage other organs. If the overproduction of cytokines does not abate, the patient may die. Diuretics and other similar drugs are used to try to ease the burden on the lungs and body in hopes that the cytokine overproduction returns to normal. Immune suppressants such as prednisone drugs have been tried with mixed results. They do suppress the overproduction of cytokines, but they also suppress the immune system in general. There is significant danger of a bacterial or another kind of viral infection occurring in the damaged tissues if the immune system is oversuppressed.

The half-life of most cytokines is minutes to hours. The cells that, produce them must be constantly stimulated to produce them. One of these tachykinins, substance P, has been shown to be a major pro-inflammatory mediator. "*Induction of Tachykinin Production in Airway Epithelia in Response to Viral Infection*," (Stewart, J. et al) PLOS ONE, Mar. 5, 2008, demonstrates the initial substance P production that initiates the cytokines comes from the damage to epithelial cells. Later, substance P is produced by damaged sensory nerves in larger and more sustained amounts.

Alternative Theory of the Virulence of Viruses and Bacteria that Results in ARDS Robinson's study used NK-1 receptor knockout mice (no functional NK-1 receptors) that were exposed to the virus that caused cardiomyopathy. NK-1 receptors are located on immune cells and substance P attaches to them, activating the immune response. Even though the level of substance P was elevated 68-fold by the virus, there was no cytokine reaction. Normal mice exposed to the virus had a 60% mortality rate, and survivors had varying degrees of slight to severe heart damage. The knockout mice suffered no heart damage, and the viral load declined by 98% in 3 days.

Inventor(s) believes Robinson's experiments show the real source of virulence in these type viruses is they have evolved a mechanism to cause an extreme cytokine reaction resulting in damage to the host tissues and immune mechanisms that allow the virus to grow and reproduce. Robinson showed that if you remove all or a lot of the cytokine reaction, you remove or lessen viral virulence and host damage.

Besides the viruses, such as influenza, cardiomyopathy, COVID-19, other viruses, bacterial infections, injuries, some medical treatments, burns or any condition that causes an extreme elevation of substance P may produce a localized or generalized cytokine storm reaction.

Conditions known to be caused by substance P cytokine chronic or acute overproduction may be mitigated by sedation-level nitrous oxide/oxygen administration by inhalation. The ability to vary the concentration and time applied of nitrous oxide will provide a very flexible treatment to reduce symptoms while minimizing side effects. Clinical observation has shown that patients with symptoms of COPD and asthma, which are known to be caused by acute and chronic excessive substance P, ray be relived with about minutes of nitrous oxide, every about 4-6 hours.

In some embodiments, average duration of inhalation would vary from about one minute to about one hour, every about 4-6 hours. Duration of each treatment could vary from about one minute to about one hour. About 20 minutes per each inhalation is believed to be optimal. In general, one appointment may span about 1-4 days. For some patients, it may take about 1-4 appointments for the treatment of ARDS.

In some embodiments, the inhalation of nitrous oxide and oxygen may treat local cytokine damages resulting from localized acutely elevated level of cytokines. The localized accurately elevated level of cytokines may be caused by, for example, burns, poison ivy, and a bacterial or viral infection such as a shingles infection and a stomach virus.

Some patients that survive a moderate to severe ARDS event may have residual symptoms such as, but not limited to, shortage of breath, fatigue, migraines, loss of taste and smell, cardiac arrhythmia, and fatigue. Conscious sedation-level nitrous oxide/oxygen may mitigate or alleviate these residual symptoms after, for example, one or more treatments of sedation-levels of about 50% nitrous oxide/about 50% oxygen for about 20 minutes once a day and will mitigate or eliminate the post-ARDS symptoms. In some embodiments, average duration of inhalation for the treatment of the post-ARDS symptoms would vary from about one minute to about one hour, once a day. Duration of each treatment could vary from about one minute to about one hour. About 20 minutes per each inhalation is believed to be optimal. In general, one appointment may span about 1-4 days. For some patients, it may take about 1-4 appointments for the treatment of post-ARDS.

The use of nitrous oxide and oxygen may lower the ganglia and epithelial production of substance P. Other inhaled anesthetic may be used to suppress the production of substance P at dosages that do not cause over-sedation respiratory depression, or irritation of the lungs or other side effects. The inhaled anesthetics must be safe for patients to inhale. Such inhaled anesthetics may include, but not be limited to, halothane, isoflurane, sevoflurane, desflurane, nitrous oxide, xenon, or a combination thereof. The inhaled anesthetics are sub-classified as either volatile or non-volatile. The volatile anesthetics (e.g., halothane, isoflurane, sevoflurane and desflurane) are liquids at room temperature and require the use of vaporizers for inhalational administration. The non-volatile anesthetics (e.g., nitrous oxide and xenon) are in gas form at room temperature. The inhaled anesthetics described in embodiments of the present disclosure do not encompass anesthetics (e.g., barbiturates, ketamine, propofol) administered by injections such as an intravenous injection.

The inhaled dosage of nitrous oxide and oxygen may be from about 1% nitrous oxide/about 99% oxygen to about 70% nitrous oxide/about 30% oxygen depending on individual needs and sensitivity. Clinical indications suggest that from about 40% nitrous oxide/about 60% oxygen to about 50% nitrous oxide/about 50% oxygen would be optimal. Other inhaled anesthetics may have to be used at a different oxygen % than the nitrous oxide to produce effective clinical results. Other aforementioned inhaled anesthetics may be included in the dosage or only the specified composition may be used. In some embodiments, time of inhalation would vary from about one minute to about one hour with about 30 minutes being the optimal time frame. Duration of substance P suppression may be from about 1 minute to about 12 hours with average cases of about 4-6 hours of substance P suppression. Depending on the level of substance P, the nitrous oxide and oxygen may be administered to a patient before, during, and/or after ARDS occurs between about for about 1 minute to about 12 hours every about 4-6 hours and optionally with continuous administration over the period of time. The nitrous oxide/oxygen mechanism is suppression of substance P in the peripheral ganglia.

In general, a composition, a duration, an interval, and a total amount of the inhaled nitrous oxide and oxygen administered to an adult, or a child is adjusted for age, weight, or a combination thereof. In particular, the amount of nitrous oxide used, duration of inhalation, and length of effectiveness will have to be titrated to the individual. For example adjustments will have to be made for age and body weight.

If side effects from too much substance P suppression nitrous oxide use Occur, then inhalation may be reduced or eliminated. Before, during, and after the provision of the inhaled nitrous oxide and oxygen, blood tests may be done to monitor and assess the patient's cytokine level including a substance P level and a viral load. In addition, before, during and after the inhalation of nitrous oxide and oxygen, a blood oxygen level and a pulse may be monitored and assessed.

In some embodiments, a composition administered to a patient consists of nitrous oxide and oxygen.

In some embodiments, a pharmaceutically active composition contained in a composition administered to a patient consists of nitrous oxide and oxygen. The composition may additionally include a pharmaceutically inactive composition such as a pharmaceutically inactive excipient, stabilizer and/or carrier.

In some embodiments, a composition administered to a patient consists essentially of nitrous oxide and oxygen. The language "consists essentially of" excludes materials (that contribute to the treatment) that materially mitigate cytokine overproduction and thereby affecting the treatment of ARDS or post-ARDS symptoms.

In some embodiments, a composition administered to a patient comprises nitrous oxide and oxygen. The composition may further comprise one or more additional pharmaceutically active ingredients. The composition may further comprise one or more additional pharmaceutically inactive ingredients.

The following non-limiting examples provide those of ordinary skill in the art with possible case scenarios and specific methods to treat conditions within the scope of embodiments of the present disclosure and are not intended to limit the scope of embodiments of the present disclosure.

Other conditions may cause ARDS by inflicting direct damage to cells. The conditions include but are not limited to burns, sickle cell anemia, water inhalation, G6PD deficiency, acute pancreatitis. No matter what causes the acute cytokine reaction (ARDS), the treatment should mitigate the effects.

Case Study

The following is a case study of a 69-year-old Hispanic female who weighs about 175 lbs. She contacted severe case of COVED-19. She refused to seek medical attention because a friend of hers died after 2 months in the hospital on a ventilator from ARDS. Ten days after being diagnosed with a positive COVID-19 test, she started the nitrous oxide treatment. At the beginning of treatment, her oxygen saturation was 85% and her pulse was 92.

She was administered by inhalation 50% nitrous oxide/50% oxygen for 20 minutes every 6 hours for 4 days. No other medication has been administered to her during the treatment. After 4 days, her blood oxygen readings were consistently in the mid-high 90s and her pulse was in the high 60s to low 70s. No symptoms including post treatment virus related conditions were retained afterwards.

An additional patient testing is being pursued for different patients and different symptoms for a better understanding of the effects of nitrous oxide and oxygen in treating ARDS and post-ARDS symptoms.

Unless defined otherwise, all technical and scientific terms used herein have same meaning as commonly understood by the person of ordinary skill in the art to which this disclosure belongs.

It should be understood that the above description of the present disclosure and specific examples, while indicating preferred embodiments of the present disclosure, are given by way of illustration and not limitation. Many changes and modifications within the scope of embodiments of the present disclosure may be made without departing from the spirit thereof, and embodiments of the present disclosure includes all such changes and modifications.

What is claimed is:

1. A method of treating ARDS (Acute Respiratory Distress Syndrome) caused by conditions that have resulted in acute overactivation of a cytokine system, in a patient in need thereof, comprising:

administering a composition comprising nitrous oxide and oxygen in gas form to the patient by inhalation before, during, and/or after ARDS occurs, thereby treating ARDS; wherein a composition of the nitrous oxide and oxygen is from about 1% nitrous oxide/about 99% oxygen to about 70% nitrous oxide/about 30% oxygen.

2. The method of claim 1, wherein the composition of the nitrous oxide and oxygen is from about 40% nitrous oxide/about 60% oxygen to about 50% nitrous oxide/about 50% oxygen.

3. The method of claim 2, wherein the composition of the nitrous oxide and oxygen is about 50% nitrous oxide/about 50% oxygen.

4. The method of claim 1, wherein the nitrous oxide and oxygen are administered to an adult who weighs about 150 lbs. for about between 1 minute and about 1 hour every about 4-6 hours.

5. The method of claim 4, wherein the nitrous oxide and oxygen are administered to an adult who weighs about 150 lbs. for about 20 minutes every about 4-6 hours.

6. The method of claim 4, wherein the administration is continuous administration over the period of time.

7. The method of claim 4, wherein a composition, a duration, an interval, and a total amount of the nitrous oxide and oxygen administered to an adult or a child is adjusted for age, weight, or a combination thereof.

8. The method of claim 1, wherein the conditions comprise a viral infection, a bacterial infection, an injury, a burn, water inhalation, a medical treatment, acute pancreatitis, G6PD deficiency, sickle anemia that have resulted in acute overactivation of a cytokine system.

9. The method of claim 1, further comprising:

conducting a blood test of the patient to monitor and/or assess the patient's cytokine level; and/or monitoring or assessing a blood oxygen level or a pulse of the patient.

10. The method of claim 1, further stopping or reducing a localized cytokine-mediated tissue injury.

11. A method of treating post-ARDS symptoms that remain after acute overactivation of a cytokine system, in a patient in need thereof, comprising:

administrating a composition comprising nitrous oxide and oxygen in gas form to the patient by inhalation, thereby treating post-ARDS symptoms;

wherein a composition of the nitrous oxide and oxygen is from about 1% nitrous oxide/about 99% oxygen to about 70% nitrous oxide/about 30% oxygen.

12. The method of claim 11, wherein the composition of the nitrous oxide and oxygen is from about 40% nitrous oxide/about 60% oxygen to about 50% nitrous oxide/about 50% oxygen.

13. The method of claim 12, wherein the composition of the nitrous oxide and oxygen is about 50% nitrous oxide/about 50% oxygen.

14. The method of claim 11, wherein the nitrous oxide and oxygen are administered to an adult who weighs about 150 lbs. for between about 1 minute and about 1 hour once a day.

15. The method of claim 14, wherein the nitrous oxide and oxygen are administered to an adult who weighs about 150 lbs. for about 20 minutes once a day.

16. The method of claim 14, wherein the administration is continuous administration over the period of time.

17. The method of claim 14, wherein a composition, a duration, an interval, and a total amount of the nitrous oxide and oxygen administered to an adult or a child is adjusted for age, weight, or a combination thereof.

18. The method of claim 11, wherein the post-ARDS symptoms comprise a viral infection, a bacterial infection or an injury that remains after acute overactivation of a cytokine system.

19. The method of claim 11, further comprising:

conducting a blood test of the patient to monitor and/or assess the patient's cytokine level; and/or monitoring or assessing a blood oxygen level or a pulse of the patient.

20. The method of claim 11, further treating local cytokine damages caused by the conditions.

21. The method of claim 1, wherein the composition administered consists essentially of nitrous oxide and oxygen in gas form.

22. The method of claim 11, wherein the composition administered consists essentially of nitrous oxide and oxygen in gas form.

* * * * *